(12) United States Patent
Ducrocq (10) Patent No.: US 7,462,218 B2
(45) Date of Patent: Dec. 9, 2008

(54) ALUMINUM MELTING METHOD USING ANALYSIS OF FUMES COMING FROM THE FURNACE

(75) Inventor: Jean Ducrocq, Bazoche-sur-Guyonne (FR)

(73) Assignee: L'Air Liquide, Societe Anonyme a Directoire et Conseil de Surveillance pour l'Etude et l'Exploitation des Procedes Georges Claude, Paris (FR)

( * ) Notice: Subject to any disclaimer, the term of this patent is extended or adjusted under 35 U.S.C. 154(b) by 596 days.

(21) Appl. No.: 10/497,454

(22) PCT Filed: Nov. 7, 2002

(86) PCT No.: PCT/FR02/03819

§ 371 (c)(1),
(2), (4) Date: Dec. 27, 2004

(87) PCT Pub. No.: WO03/056044

PCT Pub. Date: Jul. 10, 2003

(65) Prior Publication Data

US 2005/0103159 A1    May 19, 2005

(30) Foreign Application Priority Data

Nov. 29, 2001 (FR) .................................. 01 15445

(51) Int. Cl.
 *C22B 21/00* (2006.01)
(52) U.S. Cl. .......................................... 75/385; 75/678
(58) Field of Classification Search .................. 75/385, 75/678, 672
See application file for complete search history.

(56) References Cited

U.S. PATENT DOCUMENTS

| 3,759,702 A | 9/1973 | Horak |
| 5,563,903 A | 10/1996 | Jebrail et al. |
| 2002/0031737 A1* | 3/2002 | Von Drasek et al. .......... 431/79 |
| 2007/0171954 A1* | 7/2007 | Lucas et al. .................. 373/153 |

FOREIGN PATENT DOCUMENTS

| EP | 0 962 540 A1 | 9/1998 |
| WO | WO 01/33200 A1 * | 5/2001 |

* cited by examiner

*Primary Examiner*—Scott Kastler
(74) *Attorney, Agent, or Firm*—Elwood Haynes (57) ABSTRACT

A process and a device for melting aluminum where solid aluminum is melted in a furnace to form aluminum melt pool. The temperature and carbon monoxide (CO) concentration of the flue gas generated in the melting process is detected and examined for variations. Using this variation information, it is determined if aluminum oxides have formed on the surface of the aluminum melt pool and if they have, the melting process is regulated accordingly.

17 Claims, 5 Drawing Sheets

ALUMINUM MELTING METHOD USING ANALYSIS OF FUMES COMING FROM THE FURNACE

BACKGROUND OF THE INVENTION

Technical Field and Prior Art

The invention relates to the field of aluminum smelting and to aluminum melting furnaces.

It applies especially to aluminum scrap recycling processes.

In the field of secondary aluminum smelting, the impossibility of being able to measure and control many phenomena and parameters during melting constitutes an obstacle to understanding the melting process and also to obtaining better performance and to establishing rules for eliminating losses during melting.

The melting takes place in rotary or reverberatory furnaces. The process may be continuous, but most furnaces work in batch mode. Charging with materials takes place via huge doors that open into the reverberatory furnaces and via the main door in rotary furnaces. To introduce large volumes of scrap, the furnace must be charged two or three times per casting cycle.

Aluminum or its alloys must be melted above the melting point. However, in order for the liquid aluminum to flow suitably during the subsequent treatment, for example in casting machines, it is necessary for the molten metal to reach a temperature level of 760° C. It is also endeavored to avoid any overheating of the melt pool, especially above 780° C., at which temperature the rate of oxidation increases considerably, almost exponentially.

During a casting cycle, there may firstly be distinguished the initial period, when the materials are solid, which allows the absorption of a large amount of heat converted into the latent heat of melting of aluminum at 660° C.

Next, when the metal is liquid, its thermal conductivity drops to half its value in the solid state. Overheating may occur, but not uniformly, owing to heat distribution problems.

Large reverberatory furnaces are relatively more sensitive to this lack of uniformity. Heat is introduced from the surface of the liquid, but the ratio of densities is such that stable stratification occurs—hot liquid is in the upper part of the melt pool and cool liquid in the lower part.

Reverberatory furnaces include additional devices, such as gas injectors or pumps intended essentially to ensure uniformity of the melt pool and allowing a more effective melting procedure to take place.

Rotary furnaces employ only their intrinsic mixing principle. Heat is transmitted by heating the refractory that rotates beneath the liquid—the heat is introduced both via the upper surface exposed to the flame and via the bottom, which is in contact with the rotating refractory. Stratification is thus destabilized.

Metal losses during melting occur not only in the oxidized layer itself, but also because liquid is trapped in the oxidized skeleton. A trapped mixture of aluminum and alumina oxides then floats on the molten liquid. Trapped aluminum may represent 20 to 80% of the mass of what is called "dross".

To obtain a good aluminum yield from recycled scrap requires losses on ignition to be limited.

Two solutions are also applied in order to reduce metal losses in the dross.

Rotary furnaces, and also certain reverberatory furnaces, are firstly charged with fluxes, these being based on salts (essentially a mixture of NaCl and KCl), which are intended to reduce the wetting of the oxide skeletons by trapped aluminum.

The other solution is regular removal of dross from the surface. Not only does the dross floating on the liquid metal represent a loss of metal, but it also constitutes a layer of insulating material covering the liquid. As this layer is formed from alumina, it has a high melting point (greater than 1300° C.)—it does not melt further, but continues to grow. Introducing heat through such an insulating layer therefore requires ever increasing power, that is to say the upper layer is overheated. As the old saying of foundrymen goes, "dross generates dross". This dross may be removed by scraping the surface—this constitutes the dedrossing procedure.

This dedrossing operation is manual or in any case not highly mechanized.

It is essentially carried out, in reverberatory furnaces, by opening the doors, thereby introducing a large amount of air into the furnace. This has two drawbacks, namely cooling (the return to the previous temperature usually requires twice the time than that during which the door is open) and inflow of oxygen from the air, which easily oxidizes the aluminum.

In addition, there exists no means for determining when the doors have to be opened for dedrossing.

The yield of metal is determined by weighing the solid scrap at entry into the furnace, with a deduction for the estimated weight of paint and coatings, and by weighing the weight of metal obtained at exit from the furnace. During the heating, such paint and coatings undergo pyrolysis, which is completed when the charge reaches 580° C.

However, these production techniques provide no indication about the moment when the dross forms and builds up during the casting cycle. As a consequence, the execution of any action, such as limiting the time spent at high temperature in order to reduce the production of this dross, relies on the operator's experience and on empirical rules obtained laboriously over a long period of time. Any conclusion relating to such an action can be drawn only on a statistical basis since the material of the scrap, by its very nature, varies in its origin and its quality.

In reverberatory furnaces, the most advanced aluminum producers use certain regulating methods, such as verification of the temperature level of the refractory by a thermocouple, which reduces the power of the burners or which causes one or more burners to be shut down, when a critical temperature level is reached. However, these operations are essentially aimed at protecting the refractory.

They do not constitute direct indication about the formation of hot spots, where oxidation takes place.

Other producers check the temperature of the liquid metal by dipping a thermocouple into the metal. When a temperature above 760° C. is detected, the power of the burners is reduced or the furnace is charged with fresh materials.

However, this is merely a local indication, and hot spots may occur at other places.

Monitoring the temperature level of the refractory or of the liquid metal is therefore not sufficient for these operations.

Moreover, all these solutions can be implemented on reverberatory furnaces, whether fixed or tilting, but they are not suitable for rotary furnaces.

Other solutions have been presented in the literature, but these are aimed in particular at avoiding oxidation by preventing the surface of the metal from coming into contact with any oxidizer.

Thus, document JP 58-227706 proposes using measurement of the CO and $H_2$ contents in the flue gases to ensure that, in a furnace for melting nonferrous metals, the fitted burners operate in substoichiometric mode within a range of values of the oxidizer flow rate/fuel flow rate ratio going from 95 to 100%.

Document EP 962 540 discloses a combustion technique for melting a metal in a furnace. According to this technique, an oxygen-containing gas is sent into the furnace so that it remains separated from the metal melt pool by the flame of the burner.

The burner then operates substoichiometrically. The influx of oxygen comes from the zone located above the flame, the latter forming a screen between the oxygen of the gas and the surface of the molten metal.

Document U.S. Pat. No. 5,563,903 describes a technique whereby an inert or nonoxidizing gas forms a screen between the surface of the molten metal (aluminum) and a combustion zone located in the upper part of the furnace.

Document U.S. Pat. No. 3,759,702 relates to a technique in which the melting takes place initially in the open air, with a mobile burner above the surface of the materials to be melted. The flame of the burner is reducing, owing to the fact that, in the burner feed, there is a slight stoichiometric excess of fuel relative to oxygen.

These techniques are either complicated to implement or unsuitable for melting in a furnace.

The problem therefore arises of finding a technique for obtaining a high metal yield in a melting furnace.

The problem also arises of how to detect the precise moment when oxidation of the metal takes place during a casting cycle.

Knowing when oxidation occurs would make it easier to regulate the combustion operations in order to reduce or control this oxidation, without it being necessary to use production statistics that reflect as much the quality of the scrap as the melting techniques themselves.

Moreover, knowing the moment when oxidation occurs and the amount of oxide formed would make it easier to decide when to implement the dedrossing operation.

SUMMARY

The invention firstly relates to a method of detecting the formation of aluminum oxides on the surface of an aluminum melt pool in an aluminum melting furnace, characterized in that the variations in CO concentration and in the temperature in the flue gases exiting the furnace are detected.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF THE PREFERRED EMBODIMENTS

The invention also relates to a method of melting aluminum, in which:
  solid aluminum is introduced into a furnace;
  the aluminum is melted, in order to form an aluminum melt pool;
  the variations in carbon monoxide (CO) concentration and the temperature in the flue gases exiting the furnace are detected;
  the formation of aluminum oxides on the surface of the aluminum melt pool is deduced therefrom; and
  the melting process is regulated depending on the formation of aluminum oxides.

While aluminum is undergoing oxidation in the furnace, the CO and temperature variations are in the same direction, or have the same sign, which allows this oxidation to be easily detected.

According to the invention, it is therefore possible to detect positive values of the product, or of the ratio, of the CO and temperature derivatives over time so as to identify the appearance of aluminum oxidation, and to do so without having to open the furnace for visual observation and without an operator having to intervene.

It is therefore possible to use the analysis of the gases given off during melting to detect the formation of oxides, this being achieved using the temperature and CO concentration signals.

Optionally, the variations in $CO_2$ and/or $O_2$ and/or $H_2O$ may also be observed.

In particular, the inflows of air into the furnace according to the change in $H_2O$ concentration may be evaluated.

The analysis of the furnace flue gases may be used as a basis for regulating a melting process by:
  adapting the combustion power density;
  or adjusting the ratio of the flow rate of oxidizer to the flow rate of fuel feeding the burners;
  or stirring the melt pool by means of pumps or by injecting liquid;
  or an indication of the fact that the level of combustion power above the stirred melt pool may or may not be increased.

Such flue gas analysis may also be used to optimize the frequency of dedrossing.

A temperature measurement, or a sampling operation conditional on the temperature, may furthermore be applied so as to distinguish between the signal variations due to oxidation and those due to pyrolysis of the paint and coatings formed on the aluminum scrap or fragments.

The invention also relates to a device for detecting the formation of aluminum oxides on the surface of an aluminum melt pool in an aluminum melting furnace, characterized in that it comprises means of detecting the CO concentration and temperature variations in the flue gases exiting the furnace.

In an alternative way of implementing the invention, the formation of aluminum oxides on the surface of an aluminum melt pool in an aluminum melting furnace is detected using means for detecting the variation in hydrogen concentration of the atmosphere above the surface of the melt pool and means for measuring the temperature in the flue gases exiting the furnace.

Such a device may furthermore include means for detecting variations in $CO_2$ and/or $H_2O$ and/or $O_2$ concentration.

Means may be provided for comparing the directions of variation in the CO concentration and in the temperature and/or for taking the product or the ratio of the temporal variations in the CO concentration and in the temperature. Means may also be provided for comparing the values of the measured CO and/or $H_2$ contents with the respective CO and/or $H_2$ contents that the burner would have produced in the absence of interaction with the charge. Such values may be established by calibrating the burner.

The invention also relates to an aluminum melting furnace, of the reverberatory or rotary type, which includes the devices and/or means as explained above.

According to the invention, variations in carbon monoxide (CO) concentration in the flue gases exiting the furnace are detected and the temperature variations in the flue gases are measured.

Figure 1:
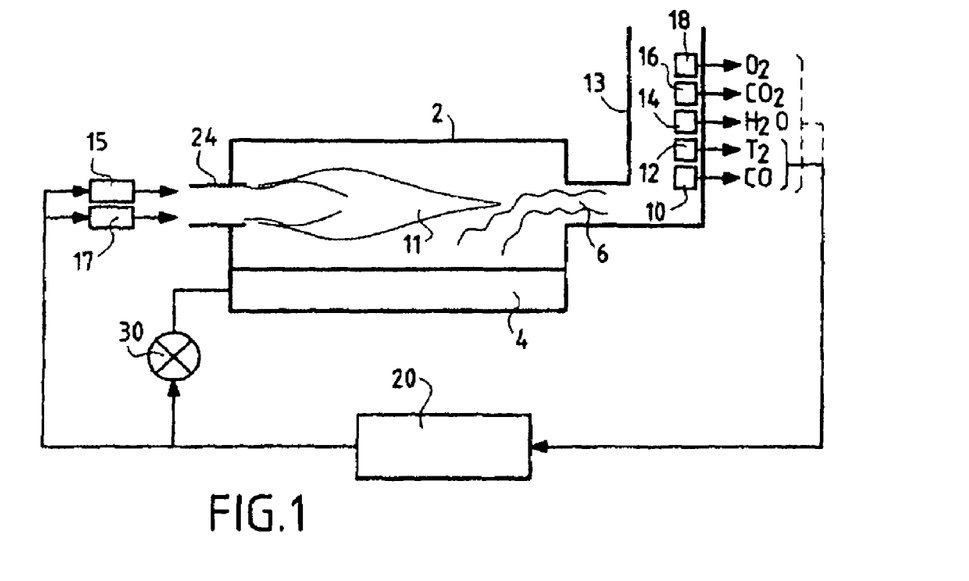
FIG. 1 illustrates one embodiment of an aluminum melting furnace according to the invention.

FIG. 1 shows schematically a furnace 2 in which an aluminum melt pool 4 is obtained by melting aluminum scrap. A burner 24, fed with an oxidizer fluid (for example oxygen) and a combustible fluid (for example a natural gas), produces a flame 11 for reaching the desired temperature in the furnace.

Several burners may also be employed.

The references 15 and 17 furthermore denote oxidizer feed means and fuel feed means, respectively.

Means 10 for measuring the variations in the amount or concentration of CO are placed at the exit of the furnace, more precisely in a flue 13 for discharging the flue gases 6.

Means 12 also allow the temperature variations to be measured at approximately the same place.

There may also be means 14, 16, 18 for measuring the water vapor ($H_2O$) and/or carbon dioxide ($CO_2$) and/or oxygen ($O_2$) concentration at the exit of the furnace, in the same flue duct.

According to one illustrative example, the measurement means 10, 14, 16, 18 may comprise one or more diode lasers, whereas the means 12 may comprise an independent thermocouple.

Figure 2:
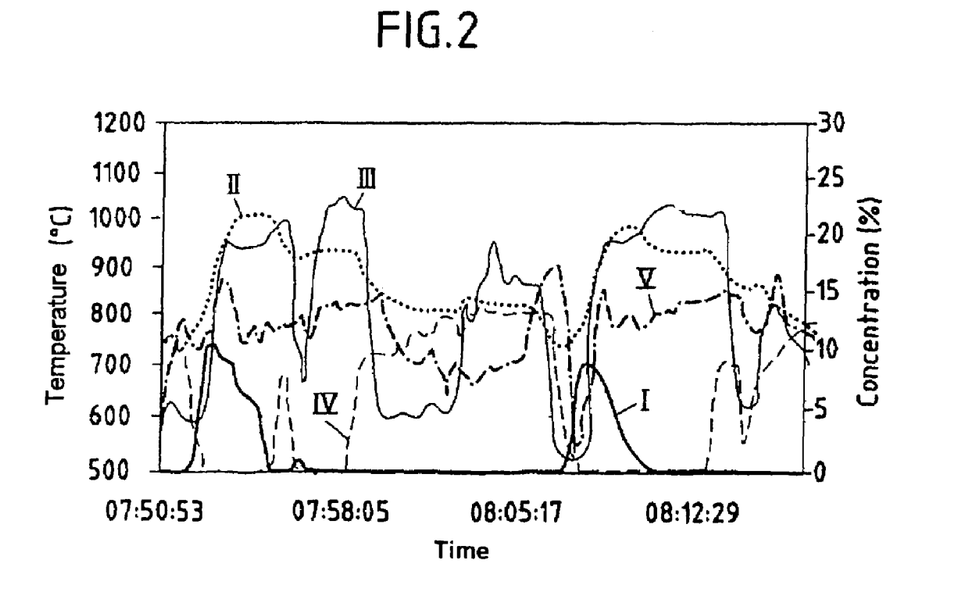
FIG. 2 illustrates the variations in temperature, CO, $CO_2$, and $H_2O$ of the flue gas.

FIG. 2 shows various curves I-V indicating, respectively, during a melting process in a dry-hearth furnace:
Curve I: the variation in carbon monoxide (CO) content;
Curve II: the variation in temperature;
Curve III: the variation in carbon dioxide ($CO_2$) content;
Curve IV: the variation in oxygen ($O_2$) content;
Curve V: the variation in water vapor ($H_2O$) content.

Curves I and II show a correlation between the CO variations and the temperature variations.

Figure 3A:
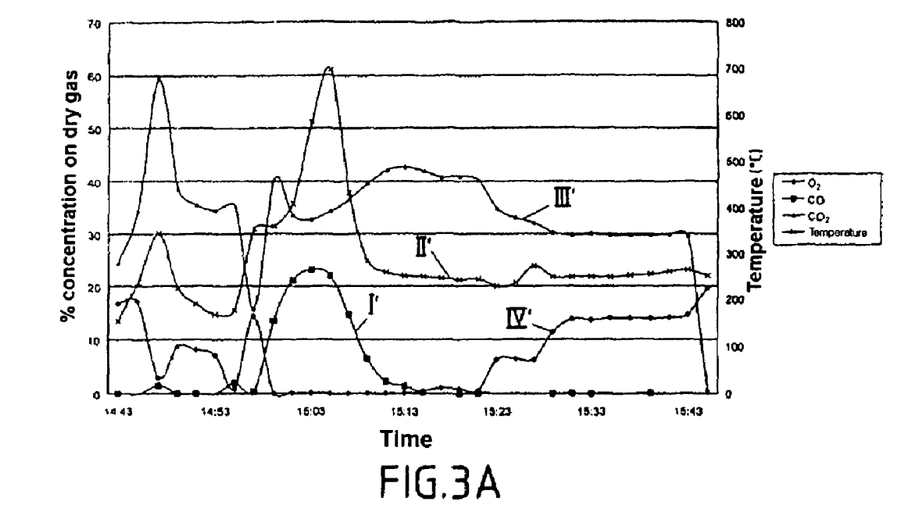
FIG. 3 illustrates measurements of temperature, CO, $CO_2$, and $H_2O$ of the flue gas, made at the exit of a rotary furnace at high and low temperature conditions.
Figure 3B:
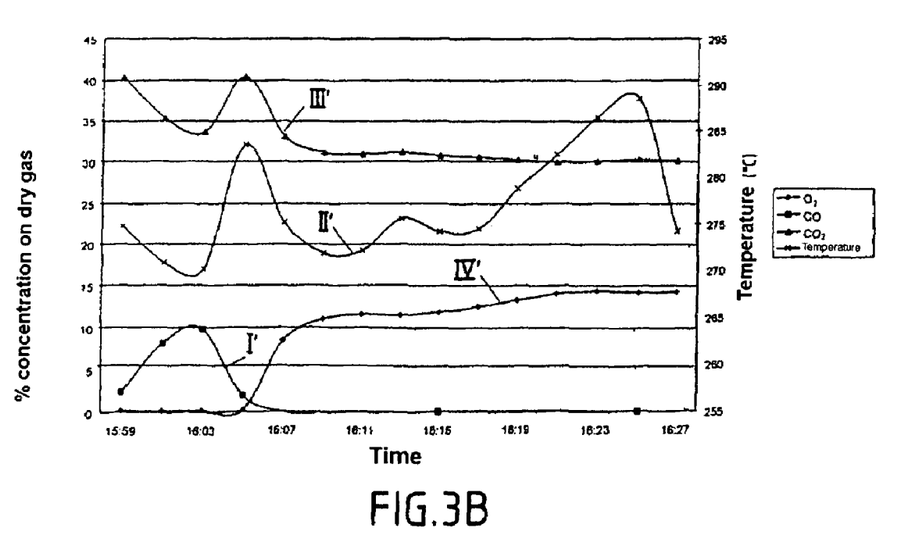

FIGS. 3A and 3B show, respectively, during a melting process in a rotary furnace:
Curve I': the variation in CO content;
Curve II': the variation in temperature;
Curve III': the variation in $CO_2$ content;
Curve IV': the variation in $O_2$ content.

FIG. 3A corresponds to the case of a high-temperature furnace and FIG. 3B to the case of a low-temperature furnace.

The conclusions allowing these measurements to be interpreted are given below. Reference will also be made to Table I below.

The composition of the combustion flue gases, essentially consisting of carbon dioxide $CO_2$ and water vapor $H_2O$, is modified by the oxidation process. Oxidation occurs not only by the action of pure oxygen or of oxygen contained in air, but also owing to the presence of $CO_2$ and water vapor $H_2O$.

In other words, oxygen ($O_2$), carbon dioxide ($CO_2$) and water vapor ($H_2O$) may interact with the aluminum charge, forming alumina.

In fact, the mass of dross produced after deducting the trapped aluminum cannot be explained by direct oxidation alone. The amount of oxygen fed in excess to the burner, increased by the air introduced into the furnace, is not sufficient for this purpose.

TABLE I

| | Variation in $H_2O$ | Mode of $O_2$-rich combustion | Mode of $O_2$-lean combustion | Sampling conditions |
|---|---|---|---|---|
| Simple combustion case | Depends only on the intake of air | No CO observed | (dCO/dt)/(dT/dt) is negative (CO/$CO_2$) is known for a given lack of $O_2$ | |
| Flue-gas/charge interaction | Below the aforementioned reference value for the same flow meter settings | 1$^{st}$ sub-case: no CO observed $CO_2$ is stable Increased in temperature 2$^{nd}$ sub-case: CO observed | (dCO/dt)/(dt/dt) is positive (CO/$CO_2$) is greater than above for fixed flow conditions | T > 400° C. (increased from 100 to 400° C. (furnace-specific value)) |

In Table I, the modes of combustion rich in oxygen ($O_2$) and lean in oxygen correspond to a burner reference signal established with respect to an empty furnace or with respect to cold aluminum. An evaluation based on the settings of the flow meters may be used as reference.

Simple combustion refers to a combustion system with no interaction with the charge (either the aluminum furnace is empty or the aluminum is cold) but with a certain air intake into the furnace. This may in all cases be hybrid combustion with air and oxygen. The water vapor ($H_2O$) concentration is then a measure of the air intake.

It may be assumed, in order to demonstrate this, that the charged scrap contains no water. Explosions due to water and to aluminum are a problem throughout the aluminum industry and the charge is stripped of any water and even moisture.

The water vapor ($H_2O$) concentration is then diluted by the air intake and may be expressed as:

air intake flow rate=theoretical flue gas flow rate[theoretical ($H_2O$)−measured ($H_2O$)/measured ($H_2O$)]

including in the case of hybrid combustion with air and oxygen; the $H_2O$ concentration is a measurement of the air intake if it is compared with the $H_2O$ content determined theoretically from knowledge of the fuel flow rate.

Given that the amount of oxygen available is determined by addition of:
the oxygen introduced by the air intake;
the oxygen measured by the flow meters (pure oxygen and added air in the hybrid or enriched combustion mode), the water vapor concentration therefore allows the amount of oxygen available for combustion to be determined.

When interaction with the charge occurs, the water vapor concentration decreases according to the equation:

$2Al+3H_2O=Al_2O_3+3H_2$, which is accompanied by the evolution of hydrogen. This phenomenon must be taken into account when evaluating the gaseous compositions on what are called "dry" flue gases, i.e. after the removal of water vapor, usually by condensation. Interaction between aluminum and water vapor increases the flow rate of dry flue gases.

The carbon monoxide (CO), carbon dioxide (CO$_2$) and temperature (T) signals in simple combustion systems can be explained as follows.

In oxygen-lean systems, carbon monoxide (CO) forms and the carbon dioxide (CO$_2$) content decreases. This is imposed by the mass constraint applied to the carbon atoms.

The CO/CO$_2$ ratio is independent of the air/oxygen combustion process. It depends only on the lack of oxygen.

The energy released in oxygen-lean systems is reduced. It is known that the maximum combustion efficiency occurs for a maximum CO$_2$ production. The signal indicates that the ratio of the CO and T variations over time (or the ratio of the derivatives with respect to time (dCO/dt)/(dT/dt)) is negative (the CO concentration increases and this increase results in poor combustion, T therefore decreasing).

When interaction with the charge occurs, and in apparent oxygen-rich conditions, either CO production is observed or a temperature increase, at constant CO$_2$, may be observed.

More precisely, when CO is given off by the reaction:

$$Al+3CO_2=Al_2O_3+3CO,$$

it burns with the addition of heat to the system (T therefore increases) according to the equation:

$$3CO+3/2O_2=3CO_2.$$

The CO combustion conditions are possibly not effective because of limited mixing of the reactants (insufficient intensity of turbulence).

The addition of heat due to the combustion process is enhanced by the exothermic nature of the reaction with aluminum. The signal is therefore such that (dCO/dt)/(dT/dt) is positive. However, it should be noted that most aluminum producers tend to work under oxygen-lean conditions. Therefore CO is produced from two sources, namely incomplete combustion and reaction with alumina Al$_2$O$_3$.

The CO produced by the burner has a defined value for a known oxygen shortage. The production of CO by oxidation is deduced from the total CO measurement less this amount produced by the burner. In addition, during an aluminum melting phase, the burner settings vary slightly. The CO variations associated with oxidation are similar to the variations in the total amount of CO.

When interaction with the charge occurs, under oxygen-lean conditions, a positive (dCO/dt)/(dT/dt) value is a clear indication of oxidation, since the reaction with alumina is exothermic.

For the same oxygen-lean setting, that is to say of the same fuel and oxidizer injection flow rate settings, (CO)/(CO$_2$) increases more quickly in the case of simple combustion. The increase in the CO/CO$_2$ ratio confirms the detection of oxidation as this ratio is independent of the hydrogen (H$_2$) content, even on dry flue gases.

It is preferable to subject a positive value of (dCO/dt)/(dT/dt) to a measurement of the temperature or to sampling conditional on the temperature.

At low temperature, some of the carbon is released from the charge by pyrolysis of the paints and coatings on the aluminum scrap, carbon monoxide (CO) then coming both from the actual combustion and from the decomposition of carbon dioxide (CO$_2$).

If the aluminum scrap has been pretreated, this pyrolysis does not take place in the furnace.

Pyrolysis takes place up to a temperature of about 580° C. At lower temperatures, CO may appear whereas oxygen may be lacking and the temperature increases.

The (dCO/dt)/(dT/dt) ratio is then positive. In fact, in such a case the combustion process is of the type:

fuel+solid carbon particles+oxygen=combustion products.

If the oxygen feed conditions remain unchanged with respect to simple combustion of the fuel, there is a lack of oxygen.

The process of pyrolyzing the paint and coatings appears to be too chaotic in the aluminum furnace for it to be followed or observed.

Consequently, a positive value of (dCO/dt)/(dT/dt) is preferably subjected to a condition on the temperature.

The latter may be measured in the liquid metal, but preferably in the flue gases, the temperature of the flue gases reflecting the temperature of the metal. A temperature difference of 100 to 400° C. allows heat transfer.

The temperature measurement may be compared with a predetermined threshold value, for example in the computer 20.

It should also be noted that, because of this correlation between the flue gas temperature and the metal temperature, it is possible for each furnace to be subjected beforehand to a learning period, the furnaces encountered in the aluminum industry varying widely.

In addition, the various modes of heat transfer do not lend themselves to an easy solution by modeling, and a learning procedure, for example based on neural networks, is possible, but not to the exclusion of a simpler measurement of the temperature difference between the metal and the flue gases.

Other conditions may in practice result in a (dCO/dt)/(dT/dt) signal with a positive value.

This is the case when the burners are operating on hot metal, which may occur for example after the burners have been shut down for a short period as a result of overheating of the refractories. In this case, the increase in temperature of the flue gases is not a reflection of a disequilibrium in the combustion or a chemical interaction with the charge, but simply an influx of energy.

However, if carbon monoxide (CO) is produced at the same time, this indicates that aluminum oxide is produced on the hot liquid metal, very probably beneath the burner.

Next, when the oxidized layer covers the liquid, the oxidation slows down and the carbon monoxide (CO) content decreases. A positive value of (dCO/dt)/(dT/dt) is then again an oxidation detector.

An alternative method of implementing the invention consists in detecting the oxidation on the aluminum surface by a direct measurement of the CO content of the flue gases from which is subtracted the CO content that the burner would have produced under similar temperature and oxidizer/fuel injection conditions in the absence of interaction with the charge.

Figure 4:
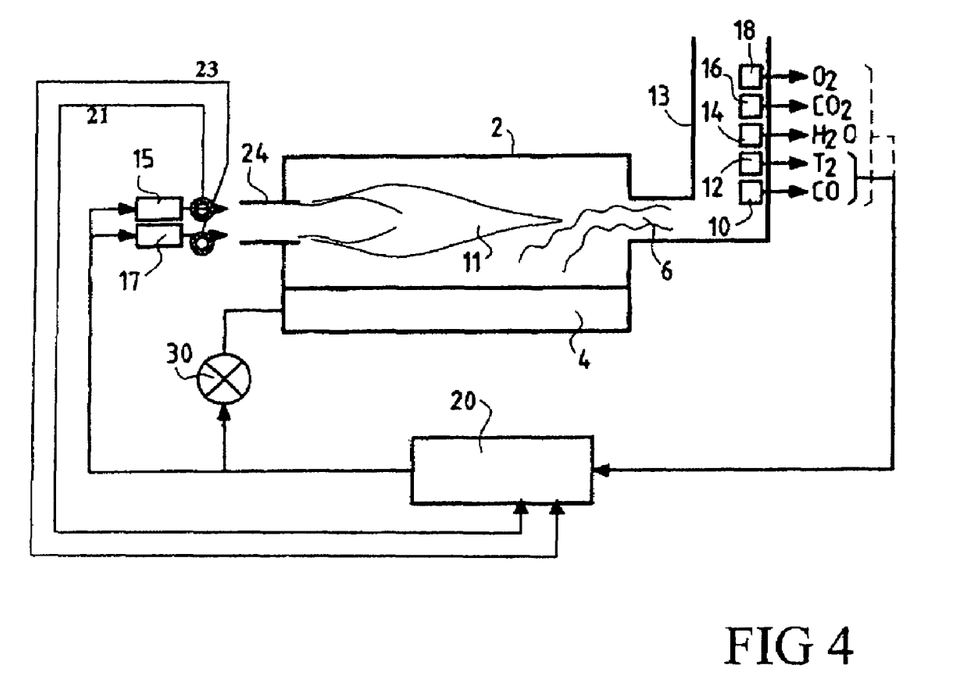
FIG. 4 illustrates one embodiment of an aluminum melting furnace according to the invention.

Practical implementation involves a device at any point similar to that shown in FIG. 1 but with the addition, to the oxidizer injection means 15, of a flowmeter 21 and, to the fuel injection means 17, of another flowmeter 23. This arrangement is shown in FIG. 4.

Initial calibration of the burner is used to determine the CO content produced by the burner alone, by recording the CO content for various injection flow rates and flue gas temperature values. Such CO values measured by the device 10 are tabulated and input into the computer 20.

These tabulated values are subtracted from the contents measured by 10 during melting of the aluminum and under the same fuel flow rate, oxidizer flow rate and flue gas temperature conditions. The value thus obtained indicates the content of CO produced by the oxidation reaction between aluminum and $CO_2$ according to the reaction:

For reasons similar to those described above, it is necessary to validate this oxidation detection by temperature-conditional sampling since the pyrolysis products given off at low temperature make the table of CO values invalid.

A third method of implementing the invention is obtained by measuring the $H_2$ content of the flue gases from which is subtracted the $H_2$ content that the burner would have produced under similar temperature and oxidizer/fuel injection conditions in the absence of interaction with the charge.

Figure 5:
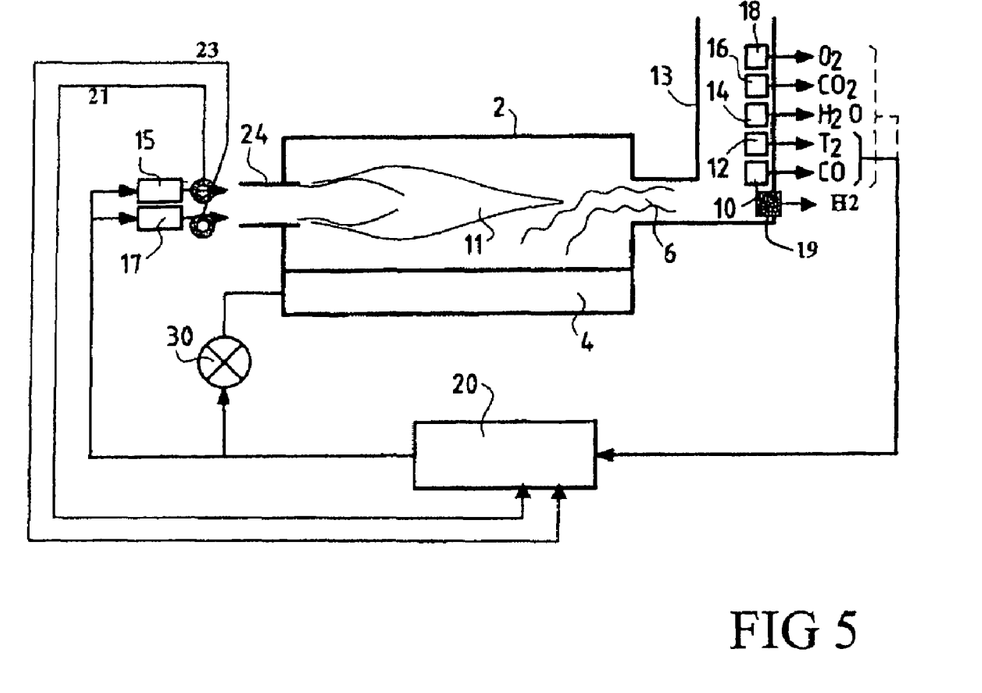
FIG. 5 illustrates another embodiment of the invention denoting the $H_2$ measuring means.

Practical implementation involves a device at any point similar to that shown in FIG. 4, but with the addition, to the flue gas composition detection means, of a means 19 for measuring the $H_2$ content. This arrangement is shown in FIG. 5.

Initial calibration of the burner is used to determine the $H_2$ content produced by the burner alone, by recording the $H_2$ content for various injection flow rates and flue gas temperature values. Such $H_2$ values measured by the device 10 are tabulated and input into the computer 20.

These tabulated values are subtracted from the contents measured by 10 during melting of the aluminum and under the same fuel flow rate, oxidizer flow rate and flue gas temperature conditions. The value thus obtained indicates the content of $H_2$ produced by the oxidation reaction between aluminum and $H_2O$ according to the reaction:

For reasons similar to those described above, it is necessary to validate this oxidation detection by temperature-conditional sampling since the pyrolysis products given off at low temperature make the table of CO values invalid.

It is preferred to measure CO rather than $H_2$ because the $H_2$ content is more difficult to measure, since hydrogen ($H_2$) is soluble in liquid aluminum, which may falsify the measurement. However, since the area for exchange between the atmosphere and the liquid metal is limited, the detection of oxidation by $H_2$ is possible since the $H_2$ measurement is clear cut as FIGS. 6a, 6b and 6c show.

Figure 6:
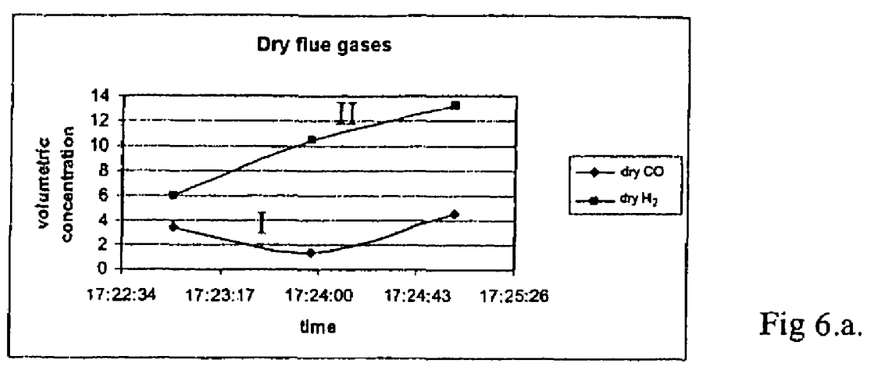
FIG. 6 illustrates CO and $H_2$ concentration measurements made at the exit of a furnace at various temperature conditions.

These FIGS. 6a, 6b and 6c show time recordings of the CO and $H_2$ concentrations during melting in a furnace fitted with a burner operating in combustion mode with oxygen. In the figures, curves I show the CO contents and curves II the $H_2$ contents. FIG. 6a corresponds to a flue gas temperature of 935° C. and FIGS. 6b and 6c correspond to a temperature of 1080° C.

The above analysis of the flue gases may be used as a basis for regulating an aluminum melting process.

After solid aluminum has been introduced into a furnace, it is melted, during which operation the carbon monoxide and temperature variations in the flue gases exiting the furnace are detected.

The signals output by the sensor 10, 12, and optionally 14, 16 and 18, may be subjected to appropriate signal processing and then used as inputs for a regulating procedure. All these operations may be carried out by means of a computer 20.

One possible regulation is that of reducing the power density of the burner 24 when oxidation is detected, the computer 20 giving, for example, a setpoint value to the feed means 15 and 17.

Another possibility is to modify the ratio of the flow rates of fuel and oxidizer delivered to the burner 24, here again by acting on the means 15 and 17. Usually, this composition is adjusted either to give the maximum power, with a slight oxygen excess (oxygen content in the flue gases between 0 and 2 to 3% oxygen), or by using, in certain producer plants, only burners operating with an oxygen-lean mixture, thus ensuring the absence of direct access of oxygen to the aluminum. Such a combustion gas atmosphere with a reducing character is obtained either by partly closing off the oxidizer injection device 15 or, if possible, by opening the fuel injection device 17 further. From an oxidizer flow rate/fuel flow rate ratio of 100%, it is possible to lower this ratio to 70%.

Covering the metals with a reducing atmosphere only after oxidation has been detected makes it possible to achieve savings as regards thermal efficiency when no combustion losses exist.

For this purpose, means (not shown in FIG. 1) may be provided for introducing such a reducing gas into the furnace, for example a supply of this gas and a duct for introducing this gas into the furnace, the opening of the duct being controlled by the computer 20 when oxidation is detected.

In fact, an oxygen-lean flame produces carbon monoxide (CO) containing some energy that is not transmitted to the charge. Highly efficient oxyburners may tolerate such a loss of energy.

Another method of regulation consists, when the onset of oxidation has been detected, in stirring the melt pool 4 using pumps 30 controlled by the computer 20.

In this case, the flue gas analysis may also indicate whether the power level of combustion above the stirred melt pool can be increased or has to be reduced.

Moreover, the flue gas analysis according to the invention and the addition of the amount of oxide produced over time can be used as a decision-making tool as regards the dedrossing operation.

Optimization of the dedrossing frequency is an advantage from the standpoint of thermal efficiency (no cooling inside the furnace until the door is opened) and as regards the yield of metal (since unnecessary access of air to the hot metal is avoided).

Finally, the analysis according to the invention, and in particular that of the water vapor ($H_2O$) concentration, can be used as a furnace diagnostic.

An air intake diagnostic is important both for thermal efficiency and for evaluating thermal equilibrium.

The invention is applicable to the aluminum smelting field. In the secondary aluminum industry, a 1% improvement in the amount of metal produced is equivalent to a 10% energy saving.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

The invention claimed is:

1. A method of melting aluminum comprising:
   a) introducing a aluminum charge into a furnace with at least one burner;
   b) melting said aluminum to form an aluminum melt pool;
   c) detecting the variations in the carbon monoxide (CO) concentration and the temperature in the flue gases;
   d) deducing the formation of aluminum oxides on the surface of said aluminum melt pool from said variations in carbon monoxide (CO) concentration and flue gas temperature; and
   e) regulating said melting process depending on said formation of said aluminum oxides.

2. The method of claim 1, further comprising detecting said variation or said formation of at least one member selected from the group consisting of:
   a) water vapor ($H_2O$);
   b) carbon dioxide ($CO_2$); and
   c) oxygen ($O_2$).

3. The method of claim 1, further comprising comparing the directions of said variations in said carbon monoxide (CO) concentration and said temperature.

4. The method of claim 1, further comprising calculating the ratio or the product of said variations in said carbon monoxide (CO) concentration and said temperature.

5. The method of claim 1, further comprising:
   a) measuring the fuel flow rate and the oxidizer flow rate;
   b) determining the ratio of said oxidizer flow rate to said fuel flow rate; and
   c) calculating the theoretical carbon monoxide (CO) content of said flue gases that said burner would have produced without any interaction with said aluminum charge.

6. The method of claim 5, further comprising:
   a) measuring the carbon monoxide (CO) content in said flue gases;
   b) subtracting the value of said theoretical carbon monoxide (CO) content from said measured carbon monoxide (CO) content; and
   c) deducing the amount of said aluminum oxide present.

7. The method of claim 1, further comprising:
   a) measuring the fuel flow rate and the oxidizer flow rate;
   b) determining the ratio of said oxidizer flow rate to said fuel flow rate; and
   c) calculating the theoretical hydrogen ($H_2$) content of said flue gases that said burner would have produced without any interaction with said charge.

8. The method of claim 7, further comprising:
   a) measuring the hydrogen ($H_2$) content in said flue gases;
   b) subtracting the value of said theoretical hydrogen ($H_2$) content from said measured hydrogen ($H_2$) content; and
   c) deducing the amount of said aluminum oxide present.

9. The method of claim 1, further comprising determining whether the temperature of said melt pool is greater than the temperature for pyrolyzing any coatings and paint on said aluminum.

10. The method of claim 1, further comprising measuring the temperature of said flue gas.

11. The method of claim 1, further comprising a means for detecting at least one member selected from the group consisting of:
    a) carbon monoxide (CO);
    b) water vapor ($H_2O$);
    c) carbon dioxide ($CO_2$); and
    d) oxygen ($O_2$).

12. The method of claim 11, wherein said means comprises at least one diode laser.

13. The method of claim 1, further comprising reducing the power of said at least one burner after detecting formation of said aluminum oxide.

14. The method of claim 1, further comprising modifying the stoichiometry of said burner after detecting formation of said aluminum oxide.

15. The method of claim 1, further comprising stirring said aluminum melt pool after detecting formation of said aluminum oxide.

16. The method of claim 1, further comprising dedrossing said surface of said aluminum melt pool after detecting formation of said aluminum oxide.

17. The method of claim 1, further comprising introducing a reducing atmosphere into said furnace after detecting formation of said aluminum oxide.

* * * * *